United States Patent [19]

Ogle, II

[11] Patent Number: 4,900,310

[45] Date of Patent: Feb. 13, 1990

[54] PROTECTIVE DEVICE FOR CANNULA USED TO DRAW BLOOD

[75] Inventor: George B. Ogle, II, Alta Loma, Calif.

[73] Assignee: International Medication Systems Limited, South El Monte, Calif.

[21] Appl. No.: 255,129

[22] Filed: Oct. 7, 1988

[51] Int. Cl.$^4$ .............................................. A61M 5/32
[52] U.S. Cl. .................................... 604/198; 604/263
[58] Field of Search ............... 128/763, 770; 604/187, 604/192, 197, 198, 263, 403, 415

[56] References Cited

U.S. PATENT DOCUMENTS

| | | | |
|---|---|---|---|
| 2,812,231 | 11/1957 | Zar | 604/415 |
| 4,425,120 | 1/1984 | Sampson et al. | 604/198 |
| 4,475,905 | 10/1984 | Himmelstrap | 604/263 |
| 4,573,976 | 3/1986 | Sampson et al. | 604/263 |
| 4,643,199 | 2/1987 | Jennings et al. | 128/763 |
| 4,643,200 | 2/1987 | Jennings | 604/198 |
| 4,723,943 | 2/1988 | Spencer | 604/198 |
| 4,772,272 | 9/1988 | McFarland | 604/198 |
| 4,790,827 | 12/1988 | Haber et al. | 128/763 |
| 4,801,295 | 1/1989 | Spencer | 604/198 |

*Primary Examiner*—Max Hindenburg
*Attorney, Agent, or Firm*—Christie, Parker & Hale

[57] ABSTRACT

A protective device for enclosing the scarf of a cannula used to draw blood includes an elongated sheath open at one end and having stop means at the other end. A piston is disposed in the sheath to be slidable between an extended position against the stop means and a retracted position away from the stop means. The piston has a bore extending through it in the direction in which the piston slides. Means are provided for securing an elongated, double-ended cannula in the piston bore so the cannula extends longitudinally through the bore with one end of the cannula in the sheath and the other end of the cannula extending outwardly away from the sheath when the piston is in the extended position. Means are provided for sliding the piston away from the stop means to the retracted position to retract the outwardly extending end of the cannula into the sheath.

14 Claims, 2 Drawing Sheets

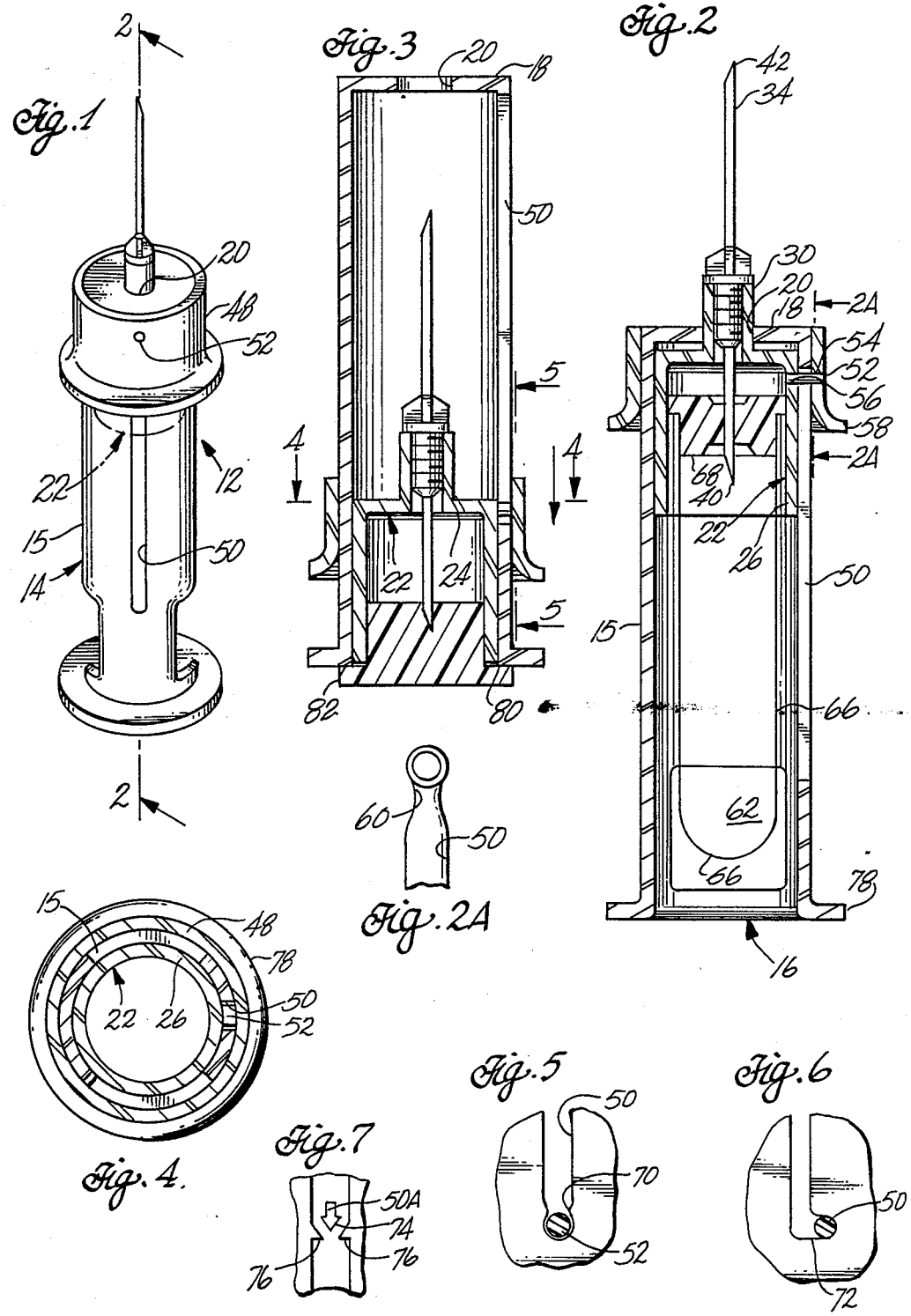

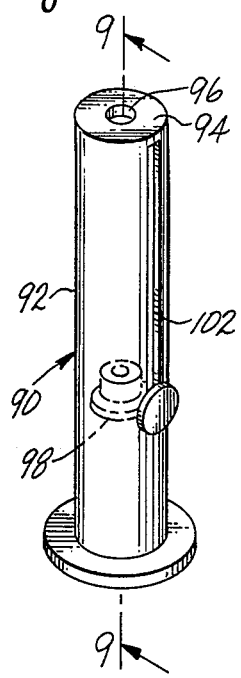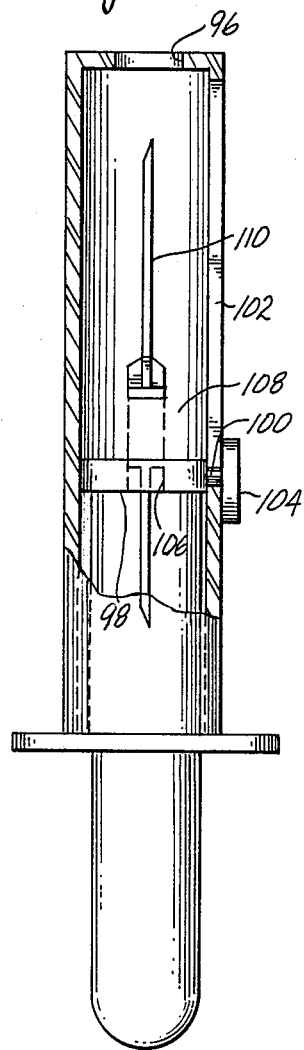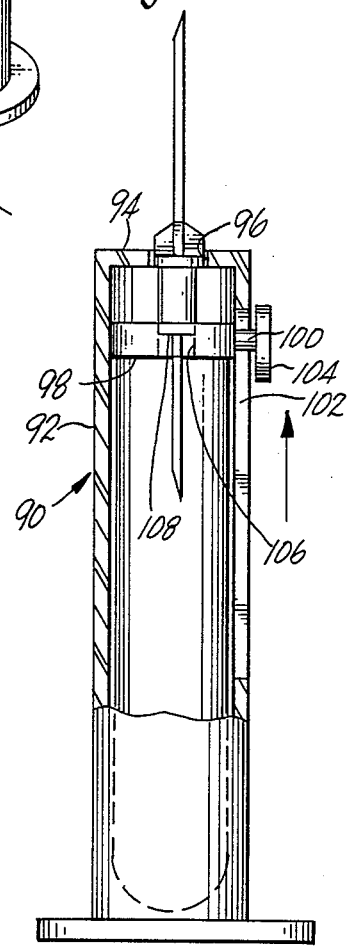

PROTECTIVE DEVICE FOR CANNULA USED TO DRAW BLOOD

BACKGROUND OF THE INVENTION

Blood samples are often taken by inserting one end of a double-ended cannula into the vein of the person or animal from which the blood sample is drawn. The other end of the cannula is inserted through a rubber stopper sealed in one end of an evacuated sample tube. The reduced pressure in the sample tube quickly draws the required amount of blood sample, and this procedure may be repeated for several stoppered tubes until the required number of separate samples are taken. Thereafter, the cannula is withdrawn from the vein, and a cotton pad or the like is pressed against the puncture wound to prevent further bleeding. After sufficient time has elapsed to ensure coagulation, the cotton pad is removed and replaced by a band-aid or the like until the puncture heals.

After the cannula is withdrawn, the exposed scarf of the cannula can result in inadvertent puncture to nurses, physicians, or technicians. In the past, such punctures were of concern because of hepatitis. However, with the onset of the acquired immune deficiency syndrome (AIDS), a puncture wound from a contaminated cannula exposes personnel to the risk of contracting AIDS, an even deadlier disease.

The present invention reduces this risk by providing a protective device which permits the cannula to be retracted into a sheath as the cannula is withdrawn from the vein. With the cannula in the retracted position, personnel are protected from inadvertent puncture by a contaminated cannula, and without having to slip a separate cover over the contaminated cannula, as has been past practice with prior art blood drawing devices.

SUMMARY OF THE INVENTION

The protective device of this invention includes an elongated sheath open at one end, and with stop means at the other end of the sheath. A piston disposed within the sheath is longitudinally slidable between an extended position against the stop means and a retracted position away from the stop means. A bore extends through the piston in the direction in which the piston slides, and means are provided for securing an elongated double-ended cannula in the piston bore so the cannula extends longitudinally through the bore with one end of the cannula in the sheath and the other end extending outwardly away from the sheath when the piston is in the extended position. Means are also provided for sliding the piston away from the extended position to the retracted position to retract the outwardly extending end of the cannula into the sheath.

In the presently preferred embodiment of the invention, the stop means includes a wall across one end of the sheath, and a bore extends through the wall to be collinear with the bore in the piston. Thus, the end of the sheath with the stop means is substantially closed, even when the piston is in the retracted position, thereby limiting the access to the sheath interior from the end covered by the wall.

Preferably, the combined length of the sheath and piston is greater than the distance between the ends of the cannula so that both ends of the cannula are fully enclosed when the piston is in the retracted position.

Preferably, the bore through the piston includes internal threads, which receive external threads on a nipple or boss secured around an intermediate portion of the cannula. In this way, when the piston is in the extended position, the cannula nipple or boss can be threaded into the piston bore to secure the cannula firmly in place.

Preferably, an annular boss around the piston bore and on the piston extends out through the sheath wall bore when the piston is in the extended position, and is internally threaded to receive the external threads on the cannula nipple.

The preferred form of the invention also includes a sleeve disposed around the sheath exterior and connected to the piston so that the sleeve may be moved longitudinally relative to the sheath to carry the piston from the extended to the retracted position. A convenient outwardly extending, annular handle on the sleeve permits an operator to slide the sleeve by using only one hand, and without concern about the orientation of the scarf, which must always be inserted in the vein with the cannula scarf oriented so the cutaway portion is visible, to be sure that the cannula opening is not plugged with skin.

In the preferred form, a pin extends from the sleeve, through a longitudinally extending slot in the sheath, and into the side of the piston so that the sleeve and piston move together. A detent adjacent the stop means receives the pin to hold the piston in the extended position with a fairly light force so the piston may easily be moved toward the retracted position. Stronger detent means are provided for the piston in the retracted piston so the piston may be securely locked in the retracted position to prevent subsequent inadvertent exposure of the contaminated cannula.

Cutouts or windows in the side of the sheath near its open end permit an operator to manipulate a sample tube which may be so short that it does not project outwardly from the open end of the sheath. Preferably, the piston carries a skirt extending away from the stop means so that when the piston is in the retracted position, the skirt covers the cutout portions in the sheath and thereby prevents inadvertent puncture from the end of the cannula adjacent the open end of the sheath.

Preferably, cap means are provided for closing the open end of the sheath after the last sample tube has been used. The cap is preferably an elastomeric material, which can easily be pierced by the adjacent end of the cannula and thus help lock the cap in place. Alternatively, the cap makes a locking fit in the open end of the sheath. A second cap may also be used to close completely the end of the sheath adjacent the stop means.

DESCRIPTION OF THE DRAWINGS

FIG. 1 is a perspective view of the presently preferred embodiment of the invention;

FIG. 2 is a view taken on line 2—2 of FIG. 1, showing the piston in the extended position;

FIG. 2A is a view taken on line 2A—2A of FIG. 2;

FIG. 3 is a view similar to FIG. 2, but showing a cap over the open end of the sheath, and showing the piston in the retracted position so the piston skirt covers side cutouts in the sheath;

FIG. 4 is a view taken on line 4—4 of FIG. 3;

FIG. 5 is a view taken on line 5—5 of FIG. 3, showing means for locking the piston in the retracted position;

FIG. 6 is a view similar to FIG. 5, showing an alternate embodiment for locking the piston in the retracted position;

FIG. 7 is another view similar to FIG. 5, showing yet another embodiment for locking the piston in the retracted position;

FIG. 8 is a perspective view of an alternate embodiment of the invention;

FIG. 9 is a view taken on line 9—9 of FIG. 8, showing the piston and cannula in the retracted position; and FIG. 10 is a view similar to FIG. 9, showing the piston and cannula in the extended position.

DESCRIPTION OF THE PREFERRED EMBODIMENTS

Referring to FIGS. 1-4, the safety device 12 includes an elongated, cylindrical sheath 14 with a cylindrical wall 15 open at one end 16 and partially closed at the other end 17 by an end wall 18 with a bore 20 extending longitudinally through the central area of the wall.

A cylindrical piston 22, with an outside diameter slightly less than the inside diameter of the sheath, is mounted within the sheath to slide longitudinally between an extended position (FIG. 2) adjacent the end wall 18 and a retracted position (FIG. 4) adjacent the open end of the sheath. The piston includes a circular end wall 24 facing the inside surface of the sheath wall 18. An annular skirt 26, formed integrally with the periphery of the piston wall 24, extends toward the open end of the sheath.

An internally threaded annular boss 30 is integrally formed with the piston wall around a central bore 32 extending longitudinally through the piston wall and boss to be collinear with the bore 20 through the sheath end wall 18.

An elongated cannula 34 is press-fitted in an externally threaded nipple 36 screwed into the internally threaded annular boss so that an inner end or scarf 40 of the cannula extends into the piston and sheath, and an outer end or scarf 42 extends outwardly away from the sheath when the piston is in the extended position shown in FIG. 2. An outwardly extending flange 44, formed integrally on the outer end of the threaded nipple, bears against the outer end of the annular boss 30 to limit the inward travel of the cannula and nipple.

An exterior sleeve 48 makes a close sliding fit around the outside of the sheath, which includes elongated and longitudinally extending slot 50 in the cylindrical wall 15.

A pin 52, perpendicular to the longitudinal axis of the sheath, is bonded or press-fitted at its outer end in a transverse bore 54 extending through the sleeve 48. The intermediate portion of the pin is disposed within slot 50, and the inner end of the pin is bonded or press-fitted in a transverse bore 56 in the piston skirt so that as the sleeve is moved longitudinally along the outside of the sheath, the pin travels in the longitudinal slot and carries the piston with the sleeve, which includes an outwardly extending annular flange or handle 58 at the end of the sleeve nearer the open end of the sheath.

As shown in FIG. 2A, the end of the slot nearer the closed end of the sheath includes a section 60 of a reduced width slightly less than the outside diameter of the pin so that as the sleeve is pushed toward the closed end of the sheath, the pin is forced through the section 60 of reduced width and held in the end of the slot, as in a detent. This is the extended position for the piston, which is held in that condition with a sufficient force to permit the cannula to be screwed in place, as shown in FIG. 2. Thereafter, a slight force exerted on the sleeve toward the open end of the sheath will force the pin past the narrow section 60 of the slot 50, all as described in more detail below.

The pin and the end of the slot adjacent the closed end of the sheath act as stop means to limit the travel of the piston away from the open end of the sheath. Alternatively, if no detent action is required, and if the end wall of the sheath is used, that end wall would serve as stop means for the piston.

A pair of diametrically opposed windows or cutouts 62 in the cylindrical wall of the sheath adjacent the open end of the sheath permit access to the closed end 64 of a cylindrical glass sample tube 66, which has an opposite open end sealed by a rubber stopper 68, which may be of conventional type.

As shown in FIG. 5, the end of the slot 50 adjacent the open end of the sheath includes a narrow section 70 of reduced width less than the diameter of the pin so that when the sleeve is forced down to the open end of the sheath, the pin 52 is jammed through the narrow section 70 of the slot with a force much stronger than that required with respect to the narrow section 60 at the other end of the slot. Thus, the sleeve and piston are substantially locked in the retracted position shown in FIGS. 3 and 5.

FIG. 6 shows an alternate embodiment in which the end of the slot at the open end of the sheath includes an L-shaped section 72, which is of slightly less width than the diameter of the pin so that as the pin is forced toward the open end of the sheath, the L-shaped section 72 of reduced width forces the pin to travel in a circumferential direction around the longitudinal axis of the sheath, securely locking the sleeve and piston against accidental displacement from the retracted position.

FIG. 7 shows yet another embodiment of the pin 50A, which in cross section looks like an arrowhead 74. The slot adjacent the open end of the sheath includes a pair of ramps 76, which extend inwardly in the direction of the open end of the sheath and form a ratchet past which the arrowhead-shaped portion of the pin may be forced and locked against accidental displacement in the opposite direction.

An outwardly extending annular flange 78 is formed around the open end of the sheath to facilitate operation of the device with one hand.

In using the safety device shown in FIGS. 1-7, the piston is moved to the extended position shown in FIG. 2. A sterile double-ended cannula, which may be of conventional type, is threaded into the annular boss 30, as shown in FIG. 2.

The outer end or scarf 42 of the cannula is inserted into a vein (not shown) from which blood is to be taken. The sample tube, sealed under vacuum by conventional means (not shown), is inserted through the open end of the sheath to the position shown in FIG. 2 so that the inner end or scarf of the cannula pierces the rubber stopper and exposes the vein interior to the reduced pressure in the sample tube. This causes a sample of blood to flow into the sample tube. After sufficient blood sample has been taken, the sample tube is withdrawn from the sheath. If the sample tube is so short that its closed end does not project outwardly from the sheath, the operator may reach the tube through the windows or cutouts 62 and work the tube off the inner end of the cannula and out of the sheath. If an additional blood sample is to be withdrawn, another sealed sample tube is inserted in the position shown in FIG. 2. That process is repeated until the required number of blood samples are taken.

The cannula is then withdrawn from the vein and retracted into the sheath by operation with one hand. This may be done by simply placing the thumb on the outwardly extending flange 78 at the open end of the sheath and placing the sleeve between the index and middle fingers. With the device held in that manner, the sleeve is then moved toward the open end of the sheath to cause the cannula to be withdrawn from the vein and safely retracted and housed within the sheath. At the same time, the operator's other hand is free to apply a cotton pad or the like to the punctured vein.

The sleeve is moved toward the open end of the sheath until the pin 52 locks in one of the detent means shown in FIGS. 5, 6, or 7. The piston and cannula are now locked in the retracted position shown in FIG. 3. The relatively small opening of the bore 20 in the end wall 18 of the sheath prevents accidental contact with the contaminated end of the cannula. With the piston in the retracted position shown in FIG. 3, the windows or cutouts are covered by the piston skirt to prevent accidental contact with the end of the cannula adjacent the open end of the sheath. For additional safety, a cap 80 may be inserted into the open end of the sheath. If desired, the cap may be a plug of material which may be penetrated by the end of the cannula adjacent the end of the sheath to hold the cap firmly in place. Alternatively, the cap may make a snug fit within the skirt to hold the cap in place without contacting the cannula. An outwardly extending flange 82, formed integrally with the cap, prevents the cap from being inserted too far into the sleeve.

In another form of the invention, the skirt may be longer than shown in FIGS. 2 and 3, or the sheath shorter, so the skirt projects beyond the open end of the sheath when the piston is in the retracted position. The combined length of the sheath and the piston skirt is greater than the distance between the ends of the cannula, so the cannula is fully sheathed when the piston and cannula are locked in the retracted position. This form of the invention provides a more compact device, with the same safe enclosure of both ends of the cannula, and also facilitates handling short sample tubes.

In the embodiment of the invention shown in FIGS. 9 and 10, an elongated sheath 90, having a cylindrical sidewall 92, is partially closed at one end by an end wall 94. A central bore 96 extends longitudinally through the sheath end wall.

A circular piston 98 makes a close sliding fit within the sheath and carries a radially extending pin 100, which extends through a longitudinal slot 102 in the cylindrical sidewall of the sheath, and is secured at its outer end to a button 104.

An internally threaded bore 106 extends longitudinally through the piston and receives an externally threaded boss or nipple 108, which carries a double-ended cannula 110, as previously described with respect to FIGS. 1-7. The cannula is mounted by moving the button 104 and piston 98 to the extended position shown in FIG. 10 so the end of the boss 108 bears against the inner face of the sheath wall. With the piston in the extended position shown in FIG. 9, the externally threaded nipple mounted on the cannula is threaded into the position shown in FIG. 9. The device is now ready for use as described with respect to the embodiment shown in FIGS. 1-7. As with the previous embodiment, the slot 102 may include suitable detent means (not shown) at each end so that the piston may be lightly held in the extended position shown in FIG. 9, and locked in the retracted position shown in FIG. 10.

I claim:

1. A protective device for a cannula used to draw blood, the device comprising:
    an elongated sheath open at one end and including a longitudinal slot;
    stop means at the other end of the sheath;
    a piston disposed in the sheath to be longitudinally slidable between an extended position against the stop means and a retracted position away from the stop means, the piston having a bore extending through it in the direction in which the piston slides;
    means for securing an elongated cannula in the piston bore so the cannula extends longitudinally through the bore with one end of the cannula in the sheath and the scarf end of the cannula extending outwardly away from the sheath when the piston is in the extended position; and
    a slidable sleeve disposed around the sheath and connected to the piston through the slot so that as the sleeve slides relative to the sheath and away from the stop means, the piston is moved longitudinally within the sheath to the retracted position and thus moves the scarf end of the cannula to a safely enclosed position within the sheath.

2. A protective device according to claim 1 in which the stop means is an end wall at the end of the sheath remote from the open end of the sheath, the end wall including a central bore extending longitudinally through it.

3. A protective device according to claim 1 or 2 in which the piston includes a skirt extending toward the open end of the sheath, and the combined length of the piston skirt and sheath is more than the distance between the ends of the cannula.

4. A protective device according to claim 1 or 2 in which the bore through the piston includes internal threads for receiving external threads provided on the cannula.

5. A protective device according to claim 1 which the sleeve includes an outwardly extending handle.

6. A protective device according to claim 1 which includes a pin extending through the slot and connected at one end to the sleeve and at the other end to the piston.

7. A protective device according to claim 6 which includes longitudinally extending detent means adjacent the end of the slot nearer the end of the sheath with the stop means for releasably holding the piston in the extended position adjacent the stop means and so the piston can be moved to the retracted position without rotating the piston relative to the sheath.

8. A protective device according to claim 7 which includes detent means in the slot adjacent the open end of the sheath for holding the piston in a retracted position adjacent the open end of the sheath.

9. A protective device according to claim 8 which includes means for locking the piston in the retracted position.

10. A protective device according to claim 1 or 2 in which the sheath includes a sidewall with at least one window at the end of the sheath remote from the stop means and in which the piston is shorter than the distance between the window and the end of the sheath with the stop means.

11. A protective device according to claim 10 which includes an annular skirt on the piston extending toward the open end of the sheath to cover the window when the piston is in the retracted position.

12. A protective device according to claim 1 or 2 which includes an annular boss on the piston and extending away from the open end of the sheath to project outwardly from the sheath when the piston is in the extended position, the annular boss being internally threaded to receive external threads on the cannula.

13. A protective device according to claim 1 or 2 in which the cannula has a scarf at each end, and which includes cap means for closing the open end of the sheath, the cap means of elastomeric material and of sufficient length to be pierced by the cannula when the piston is in the retracted position.

14. A protective device for a cannula used to draw blood, the device comprising:

an elongated sheath open at one end and including a longitudinal slot;

stop means at the other end of the sheath;

a piston disposed in the sheath to be longitudinally slidable between an extended position against the stop means and a retracted position away from the stop means, the piston having a bore extending through it in the direction in which the piston slides;

means for securing an elongated cannula in the piston bore so the cannula extends longitudinally through the bore with one end of the cannula in the sheath and the scarf end of the cannula extending outwardly away from the sheath when the piston is in the extended position;

slidable means rigidly secured to the piston and extending away from the piston through the longitudinal slot in the sheath so the slidable means and the sheath may be manipulated with one hand to move the piston away from the stop means to the retracted position so the outwardly extending scarf end of the cannula moves to a safely enclosed position within the sheath; and longitudinally extending detent means adjacent the end of the slot near the end of the sheath with the stop means for releasably holding the piston in the extended position adjacent the stop means and so the piston can be moved with one hand from the extended to the retracted position without rotating the piston relative to the sheath.

* * * * *